United States Patent [19]

Wada et al.

[11] Patent Number: 4,676,612
[45] Date of Patent: Jun. 30, 1987

[54] EYE EXAMINING APPARATUS

[75] Inventors: Shinji Wada, Kasukabe; Katsuhiko Kobayashi, Tokyo, both of Japan

[73] Assignee: Tokyo Kogaku Kikai Kabushiki Kaisha, Japan

[21] Appl. No.: 783,238

[22] Filed: Oct. 2, 1985

[30] Foreign Application Priority Data

Oct. 2, 1984 [JP] Japan ............................... 59-206774

[51] Int. Cl.⁴ ............................................. A61B 3/10
[52] U.S. Cl. ..................................... 351/211; 351/205
[58] Field of Search ................ 351/205, 211, 214, 221

[56] References Cited

U.S. PATENT DOCUMENTS 4,277,150  1/1981  Wada et al. .................... 351/211

*Primary Examiner*—Rodney B. Bovernick
*Attorney, Agent, or Firm*—Brumbaugh, Graves, Donohue & Raymond

[57] ABSTRACT

An eye examining apparatus is disclosed which is capable of the accurate detection of any abnormality in the optical system of a patient's eye which might exist at any position of the eye, and also which is capable of providing easy measurement of the degree of refraction of the patient's eye. The apparatus comprises a target projecting system for projecting onto a retina a target image to be measured; focalizing means for detecting the focus of the target to be measured and for focalizing it on the retina; and an optical transfer function measuring system for detecting the contrast of the target image to be measured, which is focalized on the retina, and thereby measuring the optical transfer function of the patient's eye.

The apparatus may further comprise means for comparing the measured optical transfer function with that of a normal eye, and the target projecting system may include a means for rotating the target image to be measured around an optical axis.

17 Claims, 6 Drawing Figures

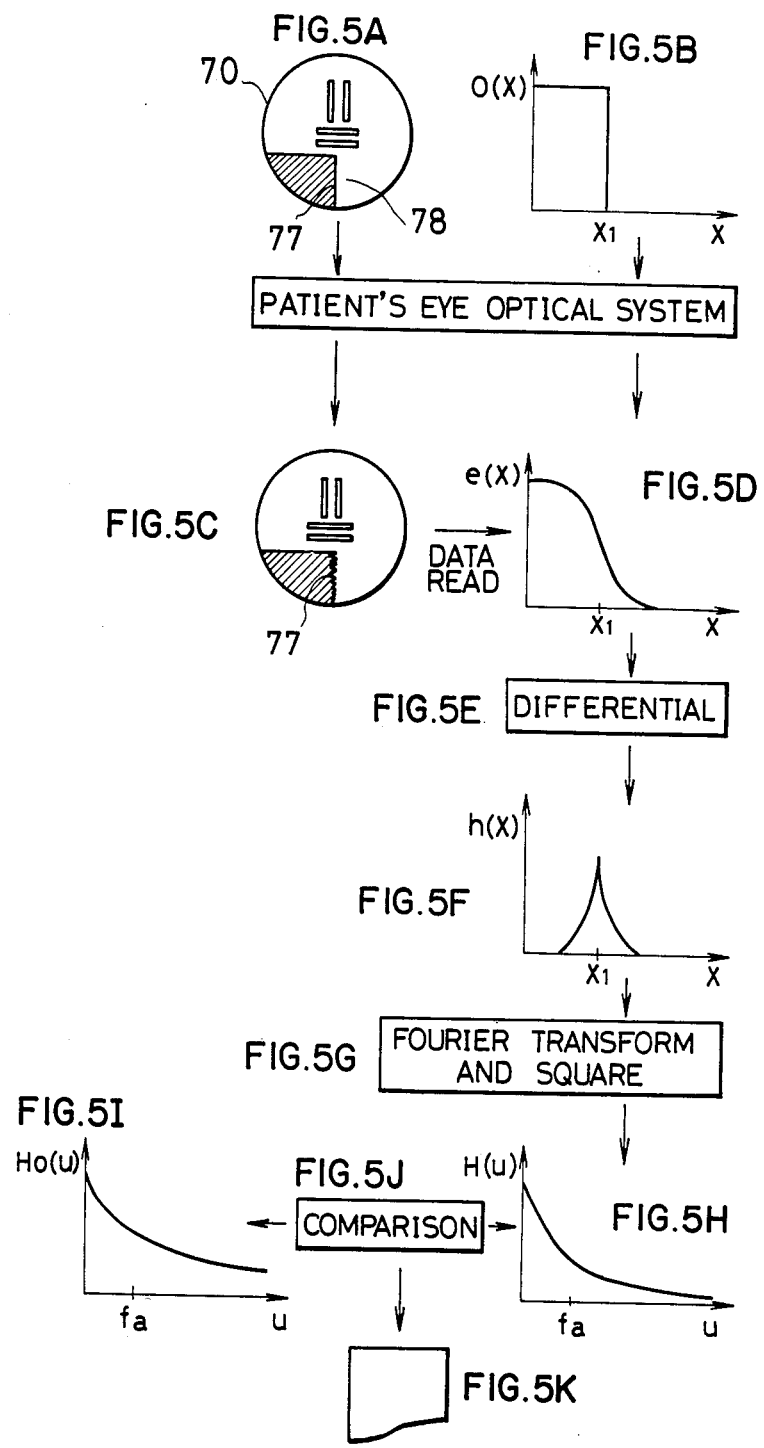

EYE EXAMINING APPARATUS

BACKGROUND OF THE INVENTION

This invention relates to an eye examining apparatus, and more particularly to an eye examining apparatus for measuring the optical transfer function of an optical system of a patient's eye.

An abnormality detecting apparatus for detecting abnormality in an optical system of a patient's eye caused by opacity of the lens or vitreous body of the patient's eye or the like by detecting the amount of reflected light, utilizing a refraction measurement system for measuring the refraction of a patient's eye, has heretofore been known as an eye examining apparatus.

As a method for examining abnormality in the optical system of an eye, a method has also been proposed or measuring the refraction across any possible diameter of a patient's eye and inferring abnormality in the optical system of the patient's eye from the scattering of these measured values.

In the above-described conventional eye examining apparatus, however, if there is opacity in the common region where both the light beam which enters the retina and the light beam reflected from the retina pass, the light beam reflected from the opacity mixes with the light beam reflected from the retina. As a result, this opacity may not be detected as abnormality in an abnormality detecting system which detects opacity of a body subject to light transmission.

Furthermore, in the method of detecting abnormality of the optical system of an eye, when opacity is generated in the vicinity of the retina of the patient's eye, the opacity has an influence on the refraction in the direction of relevant diameter, but if opacity is generated in the vicinity of the pupil, the light beam to be measured in all diametric directions passes through the opacity, so that there is no scattering of the measured values with respect to each diameter, which inconveniently makes it impossible to detect the opacity.

SUMMARY OF THE INVENTION

Accordingly, it is an object of the invention to provide an eye examining apparatus which is capable of accurate detection of abnormality in the optical system of a patient's eye which might exist at any position of the eye, thereby solving the above-described problems in the prior art.

It is another object of the invention to provide an eye examining apparatus which is capable of easy measurement of the refraction of a patient's eye.

To achieve this aim, an apparatus according to the invention is composed of a target projecting system for projecting a target image to be measured on a retina; focalizing means for detecting the focus of the target to be measured and focalizing it on the retina; and an optical transfer function measuring system for detecting the contrast of the target image to be measured which is focalized on the retina and thereby measuring the optical transfer function of a patient's eye.

In one embodiment of the invention, the target projecting system includes a means for rotating a target image to be meaured around an optical axis.

Another embodiment of the invention includes a comparing means for comparing the above-described optical transfer function with that of a normal eye.

The above and other objects, features and advantages of the present invention will become clear from the following description of the preferred embodiments thereof, taken in conjunction with the accompanying drawings.

BRIEF DESCRIPTION OF THE DRAWINGS

FIGS. 5A–5K are explanatory views of a method of calculating the optical transfer function.

DESCRIPTION OF THE PREFERRED EMBODIMENTS

Figure 1:
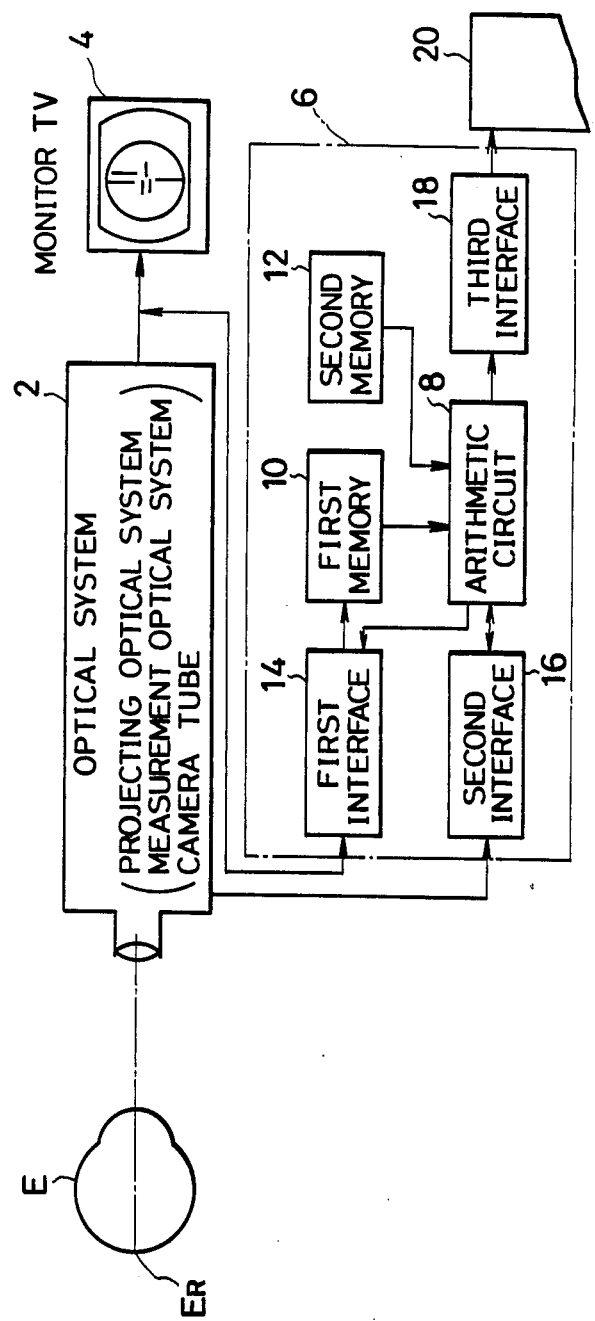
FIG. 1 is a block diagram of an embodiment of an eye examining apparatus according to the present invention.

Embodiments of an eye examining apparatus according to the invention will now be described with reference to the accompanying drawings. A first embodiment of an eye examining apparatus includes, as is shown in the block diagram of FIG. 1, an optical system 2 having an optical projecting system for projecting an image of a target plate for measuring optical transfer function on the retina $E_R$ of a patient's eye, and an optical measurement system for detecting the state of the image of the target plate formed on the retina $E_R$. The state of the image of the target plate which is detected by the optical measurement system is converted into a picture signal by camera tube and is output.

The optical system 2 is connected to a monitor TV 4 to which the picture signal is output, and the monitor TV 4 displays the image of the target plate formed on the retina $E_R$ together with the measured result which will be described later.

The electric system to which the output of the optical system 2 is input has an arithmetic circuit 8 for deciding between abnormality and normality in the optical system of the patient's eye by calculating the optical transfer function from the picture signal output from the optical system 2 and for calculating the refraction, a first memory 10 which is connected to the arithmetic circuit 8 and temporarily stores the picture signal, a second memory 12 which is also connected to the arithmetic circuit 8 and stores the optical transfer function of a normal eye, a first interface 14 which is connected to the optical system 2, the first memory 10 and the arithmetic circuit 8, a second interface 16 which is connected to the optical system 2 and the arithmetic circuit 8, and a third interface 18 which is connected to the arithmetic circuit 8 for converting the output of the arithmetic circuit 8 into a print signal.

A printer 20 for printing the output of the measured results is connected to the third interface 18.

In the above-described structure, the image of the target plate which is formed on the retina $E_R$ by the optical projecting system is projected on the camera tube and converted into a picture signal by the optical measurement system. The picture signal is input to the monitor TV 4, which displays the image of the target plate on the retina of the patient's eye. On the other hand, the picture signal is input to and stored by the first memory 10 through the first interface 14, and thereafter is input to the arithmetic circuit 8. The arithmetic circuit 8 calculates the optical transfer function from the picture signal, and decides between aberration and normality in the optical system of the patient's eye by comparing the calculated optical transfer function of the patient's eye with that of a normal eye, the result being displayed by the monitor TV 4 and printed by the printer 20.

Information about the refraction of the eye is input to the arithmetic circuit 8 through the interface 16, where the sphericity, the axis of astigmatism and the astigmatism are calculated, the results being also displayed by the monitor TV 4 and printed by the printer 20.

Figure 2:
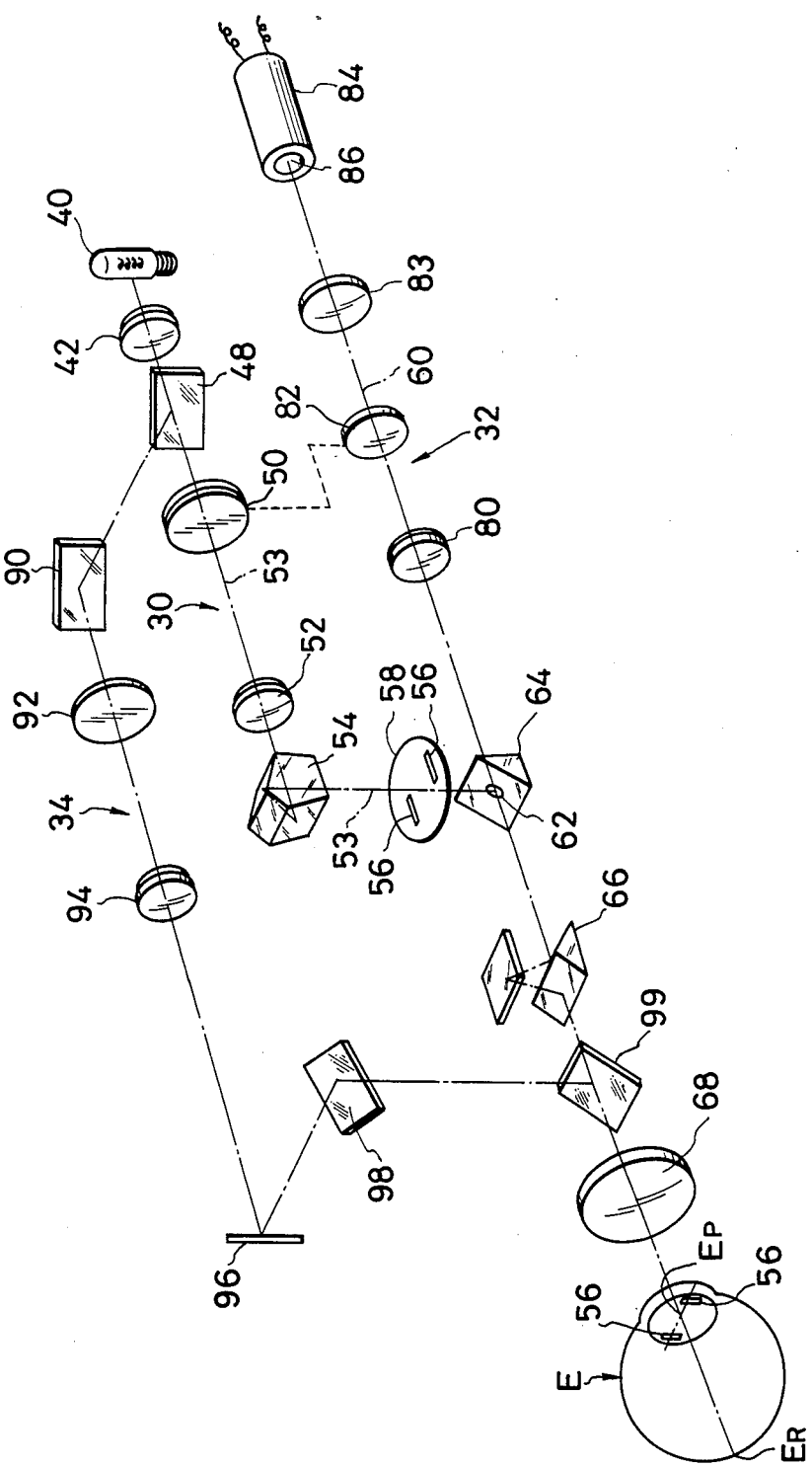
FIG. 2 shows the optical system of a refracting device.

The optical system 2 includes, as is shown in FIG. 2, an optical projecting system 30, an optical measurement system 32 and an optical fixation system 34. The optical projecting system 30 is composed of a light source 49, a condenser lens 42, an infrared-transmissing mirror 48 which is obliquely disposed before the condenser lens 42 (facing a patient's eye E) in order to take out the visible light which is to be the light beam of the light source in the optical locking system 34, a target plate 50, a projecting lens 52, a pentagonal prism 54 for refracting an optical axis 53 of the optical projecting system 30 through 90 degrees, and a stop plate 58 with rectangular openings 56 disposed away from the optical axis 53. The stop plate 58 is arranged so that it is conjugate with the light source 40 with respect to the projecting lens 52.

The optical projecting system 30 further includes a direct vision prism 64 with a through hole 62 the axis of which coincides with the optical axis 60, an image rotator 66, and an objective lens 68, all three being arranged on the optical axis 60 of the optical measurement system 32. The stop plate 58 is arranged such that it is conjugate with the pupil of a patient's eye with respect to the objective lens 68. The target plate 50 is located so that it is conjugate to the retina $E_R$ of a patient's eye in relation to the projecting lens 53 and the objective lens 68.

Figure 3:
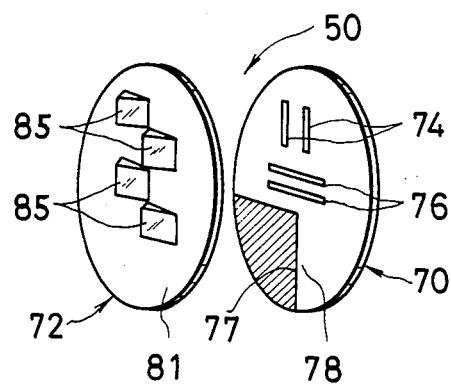
FIG. 3 is an exploded perspective view of a target plate.

The target plate 50 is, as is shown in FIG. 3, composed of a slit plate 70, and a prism plate 72 which is adjacent to the slit plate 70 and is disposed facing the patient's eye E. The slit plate 70 is composed of slits 74 for measuring the refraction and slits 76 for measuring the axis of astigmatism which are provided orthogonally to the slits 74, and a pattern 78 for the measuring optical transfer function which is divided into a section which transmits infrared light and a section which is opaque to it by a borderline 77 in the radial direction. The prism plate 72 is composed of a infrared-transmissing plate member 81, to which four prisms 85 are attached to as is shown in FIG. 3. The prisms 85 refract part of the light beam which has passed through the slits 74 for measuring the refraction and the slits 76 for measuring the axis of astigmatism in the horizontal direction viewed in FIG. 3.

In the optical projecting system 30, the light beam projected on the target plate 50 passes through the peripheral portion 56 of the pupil of the patient's eye $E_P$ and reaches the retina $E_R$. When the projected light beam is focalized on the retina $E_R$, the same pattern as that of slit plate 70 is formed thereon. When it is not focalized, the total composite image becomes unfocussed and each image of the slits 74 used for measuring the refraction is split into two. The split portions are displaced in the direction perpendicular to the slits 74 to form images.

Similarly, when the patient's eye has some astigmatism, and the direction of the slit images formed by the slits 76 for measuring the axis of astigmatism on the retina $E_R$ and the axes of astigmatism of the patient's eye do not coincident, each image of the slits 76 for measuring the axis of astigmatism is split into two, and the split parts are displaced in the direction perpendicular to the slits 76 to form images. On the other hand, when the direction of the slit images formed by the slits 76 for measuring the axis of astigmatism on the retina $E_R$ coincides with one of the axes of astigmatism of the patient's eye, the images of the slits 76 for measuring the axis of astigmatism are formed in alignment.

When the image rotator 66 is rotated, the composite image of the slit plate 70 on the retina $E_R$ rotates around the optical axis of the eye, so that the direction of the slits 76 for measuring the axis of astigmatism and the direction of the borderline 77 of the pattern 78 for measuring the optical transfer function can be made to agree with the axis of astigmatism.

The optical measurement system 32 is composed of the objective lens 68, the image rotator 66 and three image-forming lenses 80, 82 and 83. The target plate 50 in combination with the image-forming lens 82 moves along the corresponding optical axes. A camera tube 84 is disposed behind the image-forming lens 83 so that the retina $E_R$ and a light-receiving surface 86 of the camera tube 84 are conjugate with respect to the objective lens 68 and the image-forming lenses 80, 82 and 83.

In the optical measurement system 32, the light beam to be measured, which has formed the composite image of the slit plate 70 on the retina $E_R$ and is reflected therefrom, passes through the through hole 62 of the prism 64 and reaches the light receiving-surface 86. Although the image of the slit plate on the retina $E_R$ is rotated by the rotation of the image rotator 66, since the light beam to be measured is rotated by the same degrees in the opposite direction by the image rotator 66, the image of the slit plate which is constantly directed in a predetermined direction is formed on the light-receiving surface 86.

The fixation system 34 for fix visual line is composed of a mirror 90 for reflecting the light beam reflected from the infrared-transmitting mirror 48, an fixation target 92, a projecting lens 94, two mirrors 96 and 98, and an infrared-trans-mitting visible reflex mirror 99 which is provided obliquely between the image rotator 66 and the objective lens 68.

Figure 4:
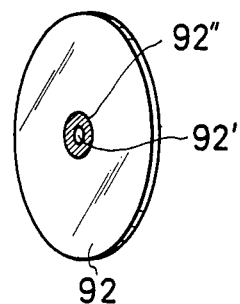
FIG. 4 is a perspective view of an oculogyric target.

The fixation target 92 is constructed so as to have only a center point 92' and a ring 92" as transmission parts, as is shown in FIG. 4, and is placed so as to have a slightly positive diopter from the position at which the fixation target 92 is conjugate with the retina $E_R$ with respect to the objective lens 68 and the projecting lens 94, in order to fogging the eye being examined.

The process of measuring by the optical system 2 will next be described. The image rotator 66, and hence the images of the slit plate on the retina $E_R$, is first rotated until the images of the slits for measuring the axis of astigmatism are aligned, while observing the composite image of the slit plate displayed on the monitor TV. This operation enables the alignment of the direction of the borderline 77 of the pattern 78 for measuring the optial transfer function with one of the axes of astigmatism.

The target plate 50 is next moved along the optical axis 53 until the images of the slits for measuring the refraction are in alignment. This operation focalizes the composite image of the slit plate 70 and forms an image on the retina $E_R$.

The image rotator 66 is next rotated in order to turn the images of the slit plate 70 on the retina $E_R$ through 90 degrees, and the target plate 50 is further moved along the optical axis 53 until the images of the slits for measuring the refraction are in alignment. This operation aligns the direction of the borderline 77 with the other axis of astigmatism, and focalizes the composite image of the split plate 70 on the retina $E_R$. It is known to those who are skilled in the art that the position of the target plate 50 and the rotation angle of the image rotator 66 in these operations can be electrically detected in at least three diametric direction and, on the basis of these detection signals, the sphericity, the astigmatism, and the axis of astigmatism can be calculated, so an explanation thereof will be omitted.

The abnormality in the optical system of the patient's eye is next detected from the picture signal of the image of the pattern 78 for measuring the optical transfer function on the retina, using the following method, while the direction of the borderline 77 of the pattern 78 for measuring the optical transfer function is in agreement with one axis of astigmatism and the images on the slit plate 70 are focalized on the retina $E_R$.

The slit plate 70 is provided with the pattern 78 for measuring the optical transfer function at its lower portion, as is shown in FIG. 5A, and the following edge function 0(X) of the borderline 77 is a step function which denotes a section which transmits infrared light and a section which is opaque to it, as is shown in FIG. 5B:

$$\text{when } 0(X) = 1: X < X_1 \atop \text{when } 0(X) = 0: X > X_1 \quad \quad (1)$$

On the other hand, in the images of the pattern 78 for measuring the optical transfer function on the retina $E_R$, the borderline 77 becomes unclear, as is shown in FIG. 5C, and its edge function e(X) is as shown in FIG. 5D. The edge function e(X) can be obtained by averaging the picture signals of a plurality of scanning lines from the camera tube 84. The line intensity spread function h(X) of the optical system of the patient's eye is obtained by differentiating the edge function e(X), as is shown in FIGS. 5(E) and 5(F), which is expressed by:

$$h(X) = \frac{d\, e(X)}{d(X)} \quad (2)$$

in which the following relationship holds:

$$e(X) = 0(X) * h(X)$$

wherein * represents convolution. The line intensity spread function h(X) obtained in this way is subjected to Fourier transform, as is shown in FIGS. 5G and 5F, and, by extractng the square root thereof, the optical transfer function H(u) which denotes the spectral intensity H(u) in the spatial frequency U of the optical system of the patient's eye can be obtained. The effects of the optical system and processing system outside the patient's eye are negligibly small, and so can be ignored.

When there is opacity in the optical systen of the patient's eye, the horderline 77 of the pattern 78 for measuring the optical transfer function becomes unclear, and the spectral intensity, namely the optical transfer function H(u), drops in the high-frequency range. The average optical transfer function Ho(u) of a normal eye is stored in the second memory 12 (FIG. 5I), and the value of {Ho(u)−H(u)} at a specific frequency, for example, that for U=fa, is calculated and compared with this function Ho(u) (FIG. 5J). When it exceeds a predetermined value, it is determined that the optical system of the patient's eye has abnormality and the result is output (FIG. 5H).

A second embodiment of the present invention is so designed as to automatically measure the sphericitiy, the astigmatism, and the axis of astigmatism and adjust the direction of the borderline of a pattern for measuring the optical transfer function. That is, the distance between the two split slit images which are separated from each other in the direction perpendicular to the slits are detected on the basis of the picture signals from the camera tube 84, a target plate 50 to be measured is automatically moved until the distance obtained by the detection signal is zero, and the degree of refraction in this diametric direction can be obtained from the amount of movement of the target plate 50. The measurement of the degree of refraction is conducted with respect to three diametric directions, and the sphericity, the astigmatism and the axis of astigmatism are calculated from these measurement results. Furthermore, on the basis of the calculation results, the borderline of the pattern for measuring the optical transfer function can be automatically made to agree with the axis of astigmatism.

In a third embodiment of the invention, the pattern for measuring the optical transfer function in the first embodiment is composed of a slit which is provided at the same position as the borderline. This embodiment enables the line intensity spread function H(X) to be obtained directly from the composite image on the retina $E_R$ in consideration of the width of the slit.

A fourth embodiment of the present invention is so composed that the edge function e(X) can be obtained by projecting the image of the pattern for measuring the optical transfer function on the retina onto a photoelectric transducer such as a two-dimendional array sensor, a one-dimensional array sensor, or a sensor utilizing mechanical scanning.

In a fifth embodiment of the present invention, the pattern for measuring the optical transfer function of the first embodiment is not provided, and the target images for measuring the degree of refraction and the axis of astigmatism are also used for measuring the optical transfer function.

Figure 6:
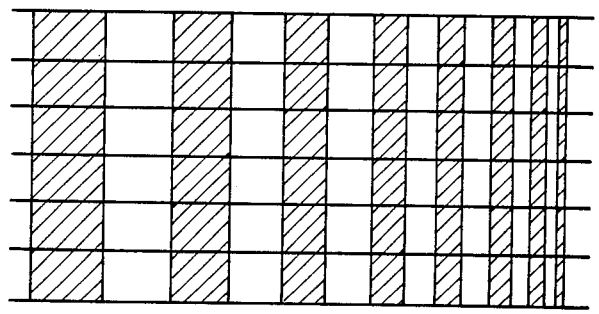
FIG. 6 schematically shows one example of a pattern for measuring the optical transfer function.

The pattern for measuring the optical transfer function in a sixth embodiment of the present invention is composed of a rectangular chart or a sine-wave chart in which frequency changes continuously, as is shown in FIG. 6. The use of this chart enables the frequency transfer function at each frequency of the optical system of the eye to be obtained without the need for a frequency analysis step.

As described above, the eye examining apparatus according to the present invention can advantageously measure the optical transfer function of the optical system of a patient's eye in the state wherein the refraction of the eye being examined is corrected and a target image to be measured is focalized by a means for focalizing the target image to be measured, so that the presence of opacity, cataracts, irregular astigmatism can be accurately detected at any position of the optical system of the patient's eye. The present invention is also advantageous in that the refraction of the eye being examined can be easily measured from the amount of adjustment of the above-described focalizing means.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An eye examining apparatus comprising:
   a target projecting system which has a target to be measured and which projects the image of said target to be measured onto the retina of a patient's eye;
   focalizing means for detecting the focus of the target image on said retina of said patient's eye and for focalizing said target image on said retina; and
   an optical transfer function measurement system for detecting the contrast of said target image from a signal output from a photoelectric detector and for measuring the optical transfer function of said patient's eye;
   said optical transfer measurement system including an optical image-forming system for projecting said target image focalized by said focalizing means onto said photoelectric detector.

2. An eye examining apparatus according to claim 1, wherein said target projecting system includes means for rotating said target image around an optical axis.

3. An eye examining apparatus according to claim 1, wherein said optical transfer function measurement system includes means for comparing a measured optical transfer function with that of a normal eye.

4. An eye examining apparatus according to claim 1, wherein said detector is a camera tube.

5. An eye examining apparatus according to claim 1, wherein said detector is a two-dimensional array.

6. An eye examining apparatus according to claim 1, wherein said detector is a one-dimensional array.

7. An eye examining apparatus according to claim 1, wherein said target to be measured is an edge pattern.

8. An eye examining apparatus according to claim 1, wherein said target to be measured is a slit pattern.

9. An eye examining apparatus according to claim 1, wherein said target to be measured is a lattice pattern.

10. An eye examining apparatus according to claim 1, wherein said target to be measured is a sine-wave pattern.

11. An eye examining apparatus according to claim 9, wherein the frequency of said lattice pattern continuously changes.

12. An eye examining apparatus according to claim 10, wherein the frequency of said sine-wave pattern continuously changes.

13. An eye examining apparatus comprising:
    a target projecting system which has a target to be measured and which projects the image of said target to be measured onto the retina of a patient's eye;
    a refraction power measurement system for detecting the focus of the target image on said retina of said patient's eye and measuring the degree of refraction of said patient's eye; and
    an optical transfer function measurement system for photoelectrically detecting the contrast of said target image focalized on said retina and for measuring the optical transfer function of said patient's eye.

14. An eye examining apparatus according to claim 13, wherein said target to be measured is composed of a target for detecting the degree of refraction and a target for detecting the axis of astigmatism.

15. An eye examining apparatus according to claim 13, wherein said target to be measured is composed of a target for detecting the degree of refraction, a target for detecting the axis of astigmatism, and a target for measuring the optical transfer function.

16. An eye examining apparatus according to claim 13, wherein said target projecting system includes means for rotating the target image around an optical axis.

17. An eye examining apparatus according to claim 13, wherein said optical transfer function measurement system includes means for comparing a measured optical transfer function with that of a normal eye.

* * * * *